(12) United States Patent
Hoeppner et al.

(10) Patent No.: US 8,396,543 B2
(45) Date of Patent: *Mar. 12, 2013

(54) STORAGE OF DATA FOR EVALUATION OF LEAD INTEGRITY

(75) Inventors: Sara M. Hoeppner, Burnsville, MN (US); Bruce D. Gunderson, Plymouth, MN (US); Amisha S. Patel, Maple Grove, MN (US); Goran Jancevski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 487 days.

This patent is subject to a terminal disclaimer.

(21) Appl. No.: 12/695,811

(22) Filed: Jan. 28, 2010

(65) Prior Publication Data

US 2011/0184481 A1 Jul. 28, 2011

(51) Int. Cl.
*A61B 5/0464* (2006.01)
(52) U.S. Cl. .................................. 600/523; 600/518
(58) Field of Classification Search .................. 600/523, 600/518; 607/14
See application file for complete search history.

(56) References Cited

U.S. PATENT DOCUMENTS

| | | |
|---|---|---|
| 4,140,131 A | 2/1979 | Dutcher et al. |
| 4,374,382 A | 2/1983 | Markowitz |
| 4,428,378 A | 1/1984 | Anderson et al. |
| 4,549,548 A | 10/1985 | Wittkampf et al. |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,201,865 A | 4/1993 | Kuehn |
| 5,215,081 A | 6/1993 | Ostroff |
| 5,224,475 A | 7/1993 | Berg et al. |

(Continued)

FOREIGN PATENT DOCUMENTS

| | | |
|---|---|---|
| GB | 2362216 A | 11/2001 |
| WO | 8901803 A1 | 3/1989 |

(Continued)

OTHER PUBLICATIONS

Written Opinion from corresponding PCT application serial No. PCT/US2010/033382 dated Feb. 1, 2012 (6 pages).

(Continued)

*Primary Examiner* — Eric D. Bertram
(74) *Attorney, Agent, or Firm* — Michael C. Soldner

(57) ABSTRACT

In general, the disclosure describes techniques for storing data corresponding to sensed high-rate non-sustained episodes that occur close in time to detection of a lead integrity condition. A method comprises detecting a first high-rate non-sustained episode, activating a data storage operation for storing data associated with high rate non-sustained episodes in response to detecting the first episode, and storing data associated with the first episode in an episode log in response to activating the data storage operation. Another method comprises detecting a lead integrity condition, and activating a data storage operation for storing data associated with high rate non-sustained episodes in response to detecting the condition.

9 Claims, 8 Drawing Sheets

U.S. PATENT DOCUMENTS

| | | | |
|---|---|---|---|
| 5,226,415 A | 7/1993 | Girodo et al. | |
| 5,292,343 A | 3/1994 | Blanchette et al. | |
| 5,312,441 A | 5/1994 | Mader et al. | |
| 5,314,450 A | 5/1994 | Thompson | |
| 5,324,315 A | 6/1994 | Grevious | |
| 5,354,319 A | 10/1994 | Wyborny et al. | |
| 5,381,803 A | 1/1995 | Herleikson et al. | |
| 5,383,909 A | 1/1995 | Keimel | |
| 5,411,530 A | 5/1995 | Akhtar | |
| 5,431,692 A | 7/1995 | Hansen et al. | |
| 5,462,060 A | 10/1995 | Jacobson et al. | |
| 5,507,746 A | 4/1996 | Lin | |
| 5,507,786 A | 4/1996 | Morgan et al. | |
| 5,534,018 A | 7/1996 | Wahlstrand et al. | |
| 5,545,183 A | 8/1996 | Altman | |
| 5,545,186 A | 8/1996 | Olson et al. | |
| 5,549,646 A | 8/1996 | Katz et al. | |
| 5,558,098 A | 9/1996 | Fain | |
| 5,564,434 A | 10/1996 | Halperin et al. | |
| 5,660,183 A | 8/1997 | Chiang et al. | |
| 5,707,398 A | 1/1998 | Lu | |
| 5,722,997 A | 3/1998 | Nedungadi et al. | |
| 5,730,141 A | 3/1998 | Fain et al. | |
| 5,741,311 A | 4/1998 | Mc Venes et al. | |
| 5,755,735 A | 5/1998 | Richter et al. | |
| 5,755,736 A | 5/1998 | Gillberg et al. | |
| 5,755,742 A | 5/1998 | Schuelke et al. | |
| 5,776,168 A * | 7/1998 | Gunderson | 607/27 |
| 5,814,088 A | 9/1998 | Paul et al. | |
| 5,868,793 A | 2/1999 | Nitzsche et al. | |
| 5,891,170 A | 4/1999 | Nitzsche et al. | |
| 5,891,179 A | 4/1999 | Er et al. | |
| 5,897,577 A | 4/1999 | Cinbis et al. | |
| 5,910,156 A | 6/1999 | Cinbis et al. | |
| 5,944,746 A | 8/1999 | Kroll | |
| 6,067,473 A | 5/2000 | Greeninger et al. | |
| 6,070,097 A | 5/2000 | Kreger et al. | |
| 6,085,118 A | 7/2000 | Hirschberg et al. | |
| 6,112,119 A | 8/2000 | Schuelke et al. | |
| 6,129,746 A | 10/2000 | Levine et al. | |
| 6,141,585 A | 10/2000 | Prutchi et al. | |
| 6,155,267 A | 12/2000 | Nelson | |
| 6,169,923 B1 | 1/2001 | Kroll | |
| 6,266,554 B1 | 7/2001 | Hsu et al. | |
| 6,317,632 B1 | 11/2001 | Krig et al. | |
| 6,317,633 B1 | 11/2001 | Jorgenson et al. | |
| 6,393,316 B1 | 5/2002 | Gillberg et al. | |
| 6,434,428 B1 | 8/2002 | Sloman et al. | |
| 6,445,952 B1 | 9/2002 | Manrodt et al. | |
| 6,477,417 B1 | 11/2002 | Levine | |
| 6,493,586 B1 | 12/2002 | Stahmann et al. | |
| 6,629,931 B1 | 10/2003 | Begemann et al. | |
| 6,650,931 B1 | 11/2003 | McClure et al. | |
| 6,658,294 B1 | 12/2003 | Zadeh et al. | |
| 6,721,600 B2 | 4/2004 | Jorgenson et al. | |
| 6,760,624 B2 | 7/2004 | Anderson et al. | |
| 6,788,971 B1 | 9/2004 | Sloman et al. | |
| 6,865,141 B2 | 3/2005 | Tada et al. | |
| 7,047,083 B2 | 5/2006 | Gunderson et al. | |
| 7,167,747 B2 | 1/2007 | Gunderson et al. | |
| 7,236,828 B2 | 6/2007 | Casavant et al. | |
| 7,266,409 B2 | 9/2007 | Gunderson | |
| 7,289,851 B2 | 10/2007 | Gunderson et al. | |
| 7,333,855 B2 | 2/2008 | Gunderson et al. | |
| 7,369,893 B2 | 5/2008 | Gunderson | |
| 7,539,540 B2 | 5/2009 | Gunderson et al. | |
| 7,567,835 B2 | 7/2009 | Gunderson et al. | |
| 2001/0031997 A1 | 10/2001 | Lee | |
| 2001/0037366 A1 | 11/2001 | Webb et al. | |
| 2002/0091333 A1 | 7/2002 | Hsu et al. | |
| 2002/0116031 A1 | 8/2002 | Vonk | |
| 2002/0118215 A1 | 8/2002 | Ball et al. | |
| 2002/0120307 A1 | 8/2002 | Jorgenson et al. | |
| 2003/0074026 A1 | 4/2003 | Thompson et al. | |
| 2003/0204215 A1 | 10/2003 | Gunderson et al. | |
| 2004/0015197 A1 | 1/2004 | Gunderson | |
| 2004/0088018 A1 | 5/2004 | Sawchuk et al. | |
| 2004/0106955 A1 | 6/2004 | Swerdlow et al. | |
| 2004/0122487 A1 | 6/2004 | Hatlestad et al. | |
| 2004/0162593 A1 | 8/2004 | Jorgenson et al. | |
| 2004/0186388 A1 | 9/2004 | Gerasimov | |
| 2004/0215270 A1 | 10/2004 | Ritscher et al. | |
| 2004/0220631 A1 | 11/2004 | Burnes et al. | |
| 2004/0230233 A1 | 11/2004 | Gunderson et al. | |
| 2004/0230242 A1 | 11/2004 | van Dam et al. | |
| 2005/0137636 A1 | 6/2005 | Gunderson et al. | |
| 2005/0154421 A1 | 7/2005 | Ousdigian | |
| 2005/0159785 A1 | 7/2005 | Rueter | |
| 2006/0074454 A1 | 4/2006 | Freeberg | |
| 2006/0116733 A1 | 6/2006 | Gunderson | |
| 2006/0235476 A1 | 10/2006 | Gunderson et al. | |
| 2008/0082012 A1 | 4/2008 | Gunderson et al. | |
| 2008/0161872 A1 | 7/2008 | Gunderson | |
| 2009/0299422 A1 | 12/2009 | Ousdigian et al. | |
| 2009/0299432 A1 | 12/2009 | Stadler et al. | |
| 2010/0058462 A1 | 3/2010 | Chow | |

FOREIGN PATENT DOCUMENTS

| | | | |
|---|---|---|---|
| WO | 97/35516 A1 | 10/1997 | |
| WO | 97/36647 A1 | 10/1997 | |
| WO | 02/24276 A1 | 3/2002 | |
| WO | 2005/056109 A1 | 6/2005 | |
| WO | 2006050360 A1 | 5/2006 | |
| WO | 2006/116430 A2 | 11/2006 | |

OTHER PUBLICATIONS

Reply to Written Opinion dated Sep. 27, 2010, from international application No. PCT/US2010/033382, filed Nov. 22, 2011, 11 pp.

International Search Report and Written Opinion of international application No. PCT/US2010/033382, mailed Sep. 27, 2010, 13 pp.

Office Action from U.S. Appl. No. 12/182,687, dated Sep. 7, 2011, 8 pp.

Response to Office Action from U.S. Appl. No. 12/182,687, filed Dec. 7, 2011, 15 pp.

International Preliminary Report on Patentability from counterpart Application Serial No. PCT/US2010/033382, dated May 15, 2012 (14 pages).

\* cited by examiner

STORAGE OF DATA FOR EVALUATION OF LEAD INTEGRITY

TECHNICAL FIELD

The disclosure relates to medical devices, and, more particularly, to medical devices that are coupled to leads to sense electrical signals within a patient and/or deliver electrical signals to a patient.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissues. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient.

Medical leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry such as signal generation and/or sensing circuitry. In some cases, the medical leads and the medical device housing are implantable within the patient. Medical devices with a housing configured for implantation within the patient may be referred to as implantable medical devices.

Implantable cardiac pacemakers or cardioverter-defibrillators, for example, provide therapeutic electrical signals to the heart via electrodes carried by one or more implantable medical leads. The therapeutic electrical signals may include pulses or shocks for pacing, cardioversion, or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

Implantable medical leads typically include a lead body containing one or more elongated electrical conductors that extend through the lead body from a connector assembly provided at a proximal lead end to one or more electrodes located at the distal lead end or elsewhere along the length of the lead body. The conductors connect signal generation and/or sensing circuitry within an associated implantable medical device housing to respective electrodes or sensors. Some electrodes may be used for both delivery of therapeutic signals and sensing. Each electrical conductor is typically electrically isolated from other electrical conductors and is encased within an outer sheath that electrically insulates the lead conductors from body tissue and fluids.

Medical lead bodies implanted for cardiac applications tend to be continuously flexed by the beating of the heart. Other stresses may be applied to the lead body, including the conductors therein, during implantation or lead repositioning. Patient movement can cause the route traversed by the lead body to be constricted or otherwise altered, causing stresses on the lead body and conductors. In rare instances, such stresses may fracture a conductor within the lead body. The fracture may be continuously present, or may intermittently manifest as the lead flexes and moves.

Additionally, the electrical connection between medical device connector elements and the lead connector elements can be intermittently or continuously disrupted. For example, connection mechanisms, such as set screws, may be insufficiently tightened at the time of implantation, followed by a gradual loosening of the connection. Also, lead pins may not be completely inserted.

Lead fracture, disrupted connections, or other causes of short circuits or open circuits may be referred to, in general, as lead integrity conditions. In the case of cardiac leads, sensing of an intrinsic heart rhythm through a lead can be altered by lead integrity conditions. Identifying lead integrity conditions may be challenging, particularly in a clinic, hospital or operating room setting, due to the often intermittent nature of lead integrity conditions. Identification of lead integrity conditions may allow modifications of the therapy or sensing, or lead replacement.

SUMMARY

In general, the disclosure is directed to techniques for storing data corresponding to sensed high rate non-sustained episodes (high-rate NS episodes) that occur close in time to identification of a lead integrity condition. High-rate NS episodes may comprise a series of rapid events detected by a medical device as intrinsic ventricular or atrial depolarizations that did not meet a criterion or criteria for classification as a tachycardia or fibrillation. A high-rate NS episode may fail to meet a criterion for classification as a tachycardia or fibrillation if, for example, the episode was too short to meet a number of intervals to detect (NID) threshold for tachycardia or fibrillation. High-rate NS episodes may be non-physiological and, instead, associated with a lead integrity condition. The storage of such episode data may help facilitate assessment of a lead in response to detection of a lead integrity condition.

A medical device may detect a lead integrity condition based on the satisfaction of one or more criteria. One example criterion for detection of a lead integrity condition is the detection of a threshold number of high-rate NS episodes, or a threshold number of high-rate NS episodes within predetermined period of time. Another example of a criterion for detection of a lead integrity condition is the detection of a threshold number of short intervals, or a threshold number of short intervals within a predetermined period of time. A short interval may be an interval between two events detected by a medical device, such as an interval between intrinsic ventricular or atrial depolarizations that is less than a threshold. Another example criterion for detection of a lead integrity condition is a determination that an impedance of a lead has exceeded or fallen below a threshold, which threshold may be a predetermined fixed threshold, or a threshold determined based on previously measured values of the impedance.

Detection of a lead integrity condition may result in, and be referred to as, a lead integrity alert. A lead integrity alert may be an alert presented to a user of a computing device that communicates with the medical device, e.g., an external programmer or other computing device that communicates with an implantable medical device. Data corresponding to sensed high-rate NS episodes that occur close in time to a lead integrity alert may help facilitate assessment of a lead in response to a lead integrity alert.

When at least one high-rate NS episode occurs, or a lead integrity condition is detected, a medical device may automatically adjust its data storage operation to provide more diagnostic data for analysis of the lead related condition. For example, the medical device may activate storage of high-rate NS episode data in a dedicated episode storage space, such as an episode log. The episode log may have a limited size and may only be capable of storing data associated with a certain number of high-rate NS episodes. The high-rate NS episode storage operation may be configured to store data associated with episodes that occur proximate to detection of a lead integrity condition.

For example, if the high-rate NS data storage operation is activated in response to the detection of a high-rate NS episode, the medical device may store data associated with high-rate NS episodes in chronological order. If the episode log reaches capacity, the oldest data may be discarded such that data associated with the most recent high-rate NS episodes are stored. When a lead related integrity is detected, the data storage operation may prevent the data stored in the episode log from being overwritten until the data is accessed for analysis. This may help ensure that data preceding the detection of the lead integrity condition is available to assess the lead integrity condition.

If the episode log is not at capacity when the lead integrity condition is detected, the data storage operation may continue storing high-rate NS episode data until the episode log is at capacity or the data is accessed for analysis. Data stored following detection of the lead integrity condition may also help facilitate evaluation of the lead related condition. If the data storage operation is activated for a threshold time period, e.g., one month, without detection of a lead integrity condition, the data storage operation may be turned off.

If the high-rate NS data storage operation is activated in response to detection of a lead integrity condition, the medical device may store data associated with high-rate NS episodes subsequent to detection of the lead integrity condition. The medical device may store such episodes until the episode log reaches capacity or the data is accessed for analysis. If the episode log reaches capacity, the data storage operation may prevent the stored data from being overwritten until the data is accessed for analysis.

In one example, a method comprises detecting a first high rate non-sustained episode, activating a data storage operation for storing data associated with high rate non-sustained episodes in response to detecting the first episode, and storing data associated with the first episode in an episode log in response to activating the data storage operation.

In another example, a method comprises detecting a lead integrity condition and activating a data storage operation for storing data associated with high rate non-sustained episodes in response to detecting the condition.

In another example, a system comprises a sensing module that monitors a signal indicative of cardiac contractions, a processor that detects a first high rate non-sustained episode based on the signal sensed by the sensing module and activates a data storage operation for storing data associated with high rate non-sustained episodes in response to detecting the first episode, and a memory that stores data associated with the first episode in response to the processor activating the data storage operation.

In another example, a system comprises a sensing module that monitors a signal indicative of cardiac contractions and a processor that detects a lead integrity condition based on the signal sensed by the sensing module and activates a data storage operation for storing data associated with high rate non-sustained episodes in response to detecting the condition.

In another example, a system comprises means for detecting a first high rate non-sustained episode, means for activating a data storage operation for storing data associated with high rate non-sustained episodes in response to detecting the first episode, and means for storing data associated with the first episode in an episode log in response to activating the data storage operation.

In another example, a system comprises means for detecting a lead integrity condition, and means for activating a data storage operation for storing data associated with high rate non-sustained episodes in response to detecting the condition.

DETAILED DESCRIPTION

Figure 1:
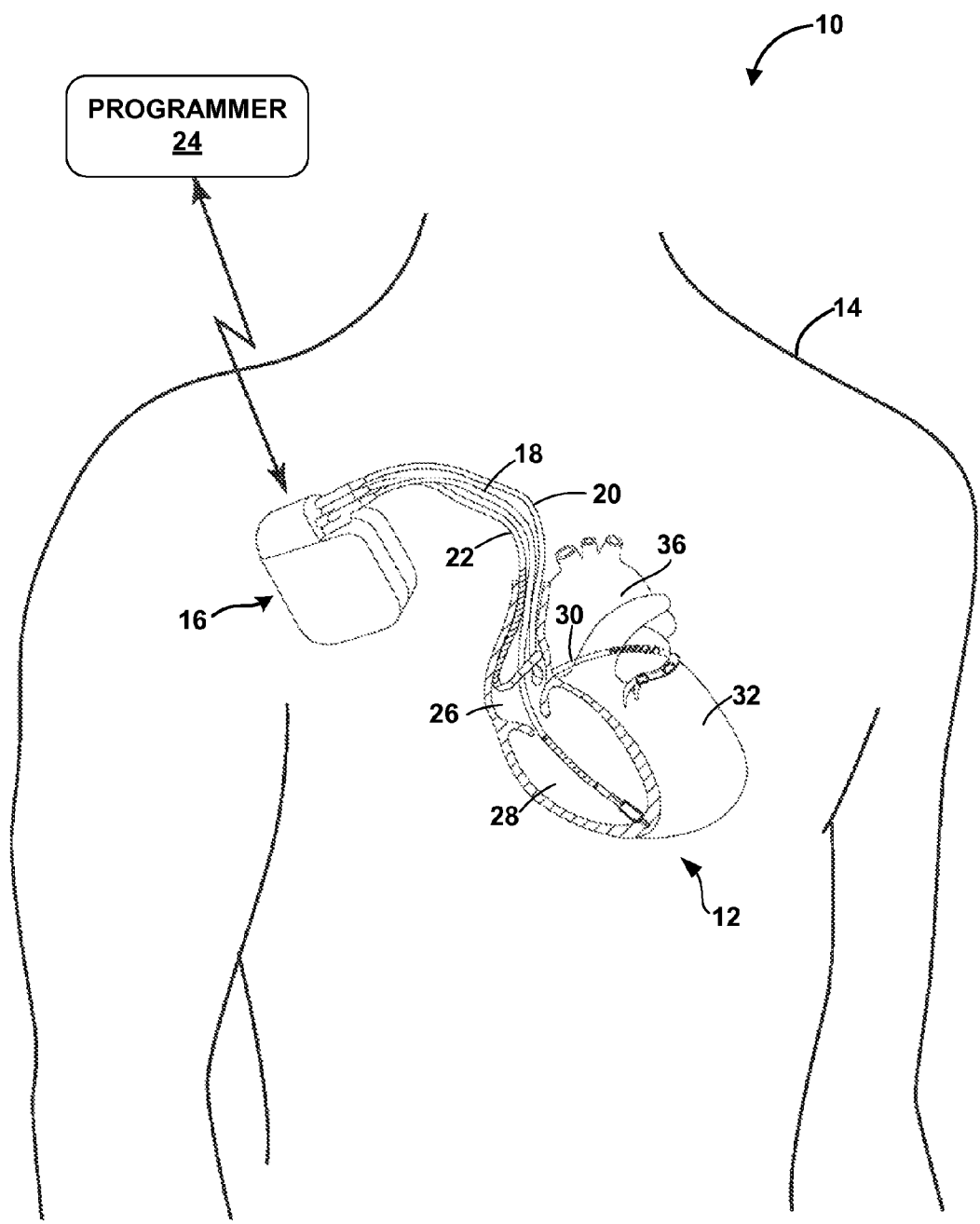
FIG. 1 is a conceptual diagram illustrating an example system that includes an implantable medical device (IMD) coupled to implantable medical leads.

FIG. 1 is a conceptual diagram illustrating an example system 10 that may be used to provide therapy to heart 12 of patient 14. System 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 12 is ordinarily, but not necessarily, a human patient.

Although an implantable medical device and delivery of electrical signals to heart 12 are described herein as examples, the techniques for storing data corresponding to sensed episodes or events that occur close in time to detection of a lead integrity condition described in this disclosure may be applicable to other medical devices and/or other therapies. In general, the techniques described in this disclosure may be implemented by any medical device, e.g., implantable or external, that includes or is coupled to leads to detect electrical signals or other physiological parameters from a patient, and/or delivers electrical signals to a patient, or any one or more components of a system including such a medical device. As one alternative example, IMD 16 may be a neurostimulator that delivers electrical signals to and/or monitor conditions associated with the brain, spinal cord, or neural tissue of patient 16.

In the example of FIG. 1, leads 18, 20, 22 extend into the heart 12 of patient 14 to sense electrical activity of heart 12 and/or deliver electrical signals to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into right atrium 26 of heart 12.

In some examples, system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, system 10 may additionally or alternatively include temporary or permanent epicardial or subcutaneous leads, instead of or in addition to transvenous, intracardiac leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing stimulation to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., shocks with increasing energy levels, until a fibrillation of heart 12 is stopped. IMD 16 may detect fibrillation employing one or more fibrillation detection techniques known in the art.

In some examples, programmer 24 comprises a handheld computing device, computer workstation, or networked computing device. Programmer 24 may include a user interface that receives input from a user. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve high-rate NS episode data stored in association with detection of a lead integrity condition, e.g., stored in association with a lead integrity alert, from IMD 16 and/or other information regarding the performance or integrity of IMD 16 or other components of system 10, such as leads 18, 20 and 22, or a power source of IMD 16. IMD 16 and programmer 24 may communicate via wireless communication using any techniques known in the art.

IMD 16 is an example of a device that may store data, such as electrograms (EGMs), corresponding to sensed episodes or events that occur close in time to the detection of a lead integrity condition, e.g., the occurrence of a lead integrity alert. Such episode data may be retrieved from IMD 16 by programmer 24, and displayed by programmer 24 for evaluation by a clinician or other user to, for example, evaluate a lead integrity condition. In some examples, IMD 16 may store EGMs in conjunction within other lead integrity data, such as lead impedance data, which may also be retrieved and displayed by programmer 24. The EGMs may be stored with respective marker channels.

In other examples, one or more devices other than IMD 16 may, alone, or in combination with IMD 16, implement the techniques described herein. For example, programmer 24 or another external device may store data corresponding to sensed episodes or events that occur close in time to detection of a lead integrity condition. Programmer 24 or another external device may determine whether to store high-rate NS episode data, according to any of the techniques described herein, based on the detection of a lead integrity condition.

Figure 2:
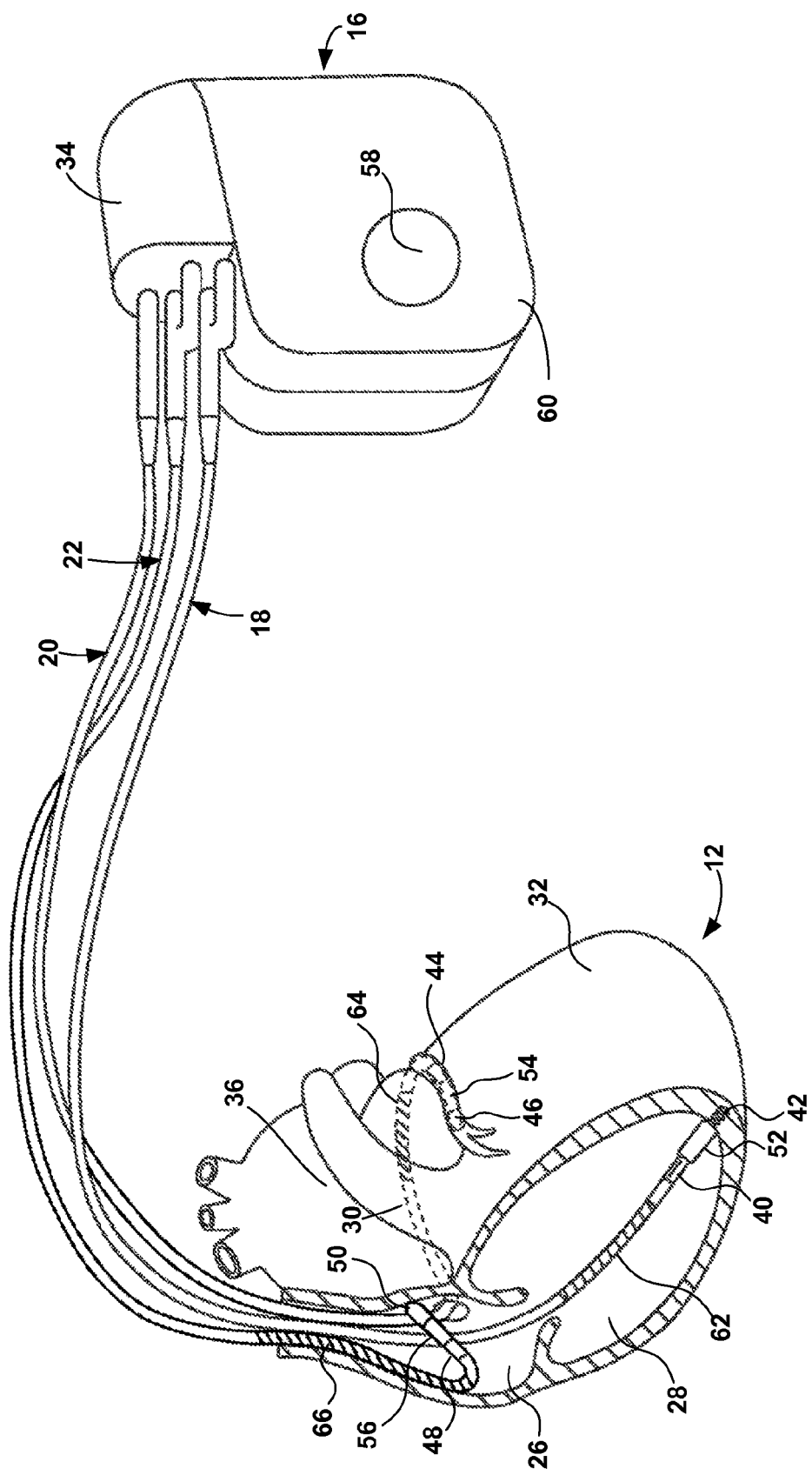
FIG. 2 is a conceptual diagram further illustrating the IMD and leads of the system of FIG. 1 in conjunction with the heart.

FIG. 2 is a conceptual diagram illustrating IMD 16 and leads 18, 20 and 22 of system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration.

In some examples, IMD 16 delivers pacing stimulation via bipolar combinations of electrodes 40, 42, 44, 46, 48 and 50 to produce depolarization of cardiac tissue of heart 12. In some examples, IMD 16 delivers pacing stimulation via any of electrodes 40, 42, 44, 46, 48 and 50 in combination with housing electrode 58 in a unipolar configuration. Furthermore, IMD 16 may deliver defibrillation shocks to heart 12 via any combination of elongated electrodes 62, 64, 66, and housing electrode 58. Electrodes 58, 62, 64, 66 may also be used to deliver cardioversion shocks to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of electrical signals or sensing, their associated conductors and connectors, and any tissue or fluid between the electrodes, may define an electrical path.

The configuration of system 10 illustrated in FIGS. 1 and 2 is merely one example. In other examples, a system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

Figure 3:
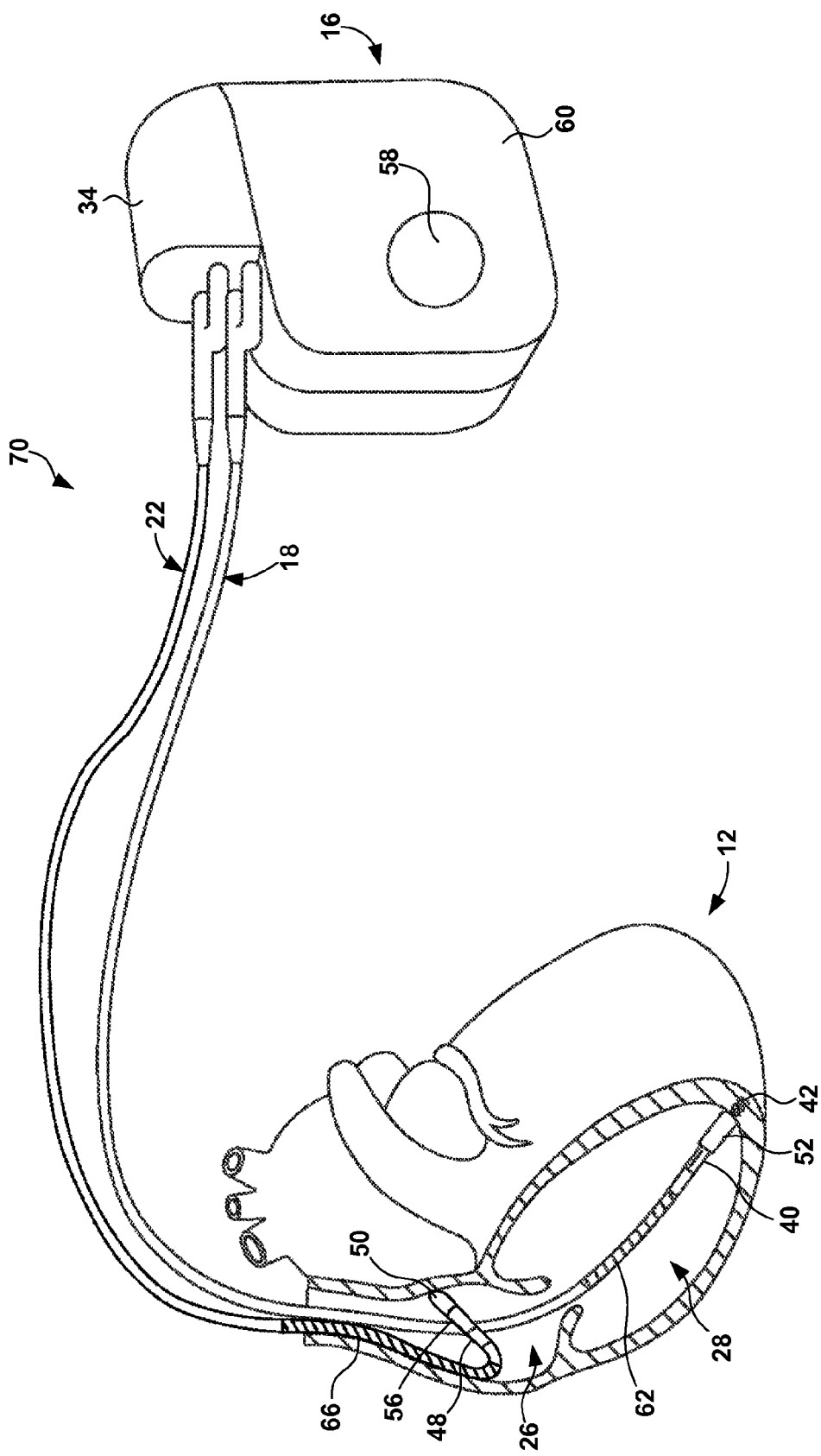
FIG. 3 is a conceptual diagram illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, other examples of systems may include three transvenous leads located as illustrated in FIGS. 1 and 2, and an additional lead located within or proximate to left atrium 36. As another example, other examples of systems may include a single lead that extends from IMD 16 into right atrium 26 or right ventricle 28, or two leads that extend into a respective one of the right ventricle 26 and right atrium 26. An example of this type of system is shown in FIG. 3. Any electrodes located on these additional leads may be used in sensing and/or signal delivery configurations.

Additionally, as previously mentioned, IMD 16 need not deliver therapy to heart 12. In general, this disclosure may be applicable to any medical device, e.g., implantable or external, that includes leads to sense electrical signals or other physiological parameters from a patient, and/or deliver electrical signals to a patient.

FIG. 3 is a conceptual diagram illustrating another example of system 70, which is similar to system 10 of FIGS. 1 and 2, but includes two leads 18, 22, rather than three leads. Leads 18, 22 are implanted within right ventricle 28 and right atrium 26, respectively. System 70 shown in FIG. 3 may be useful for providing defibrillation shocks and pacing stimulation to heart 12. The techniques for storing data corresponding to sensed episodes or events that occur close in time to detection of a lead integrity condition described this disclosure may be performed in two lead systems in the manner described herein with respect to three lead systems.

Figure 4:
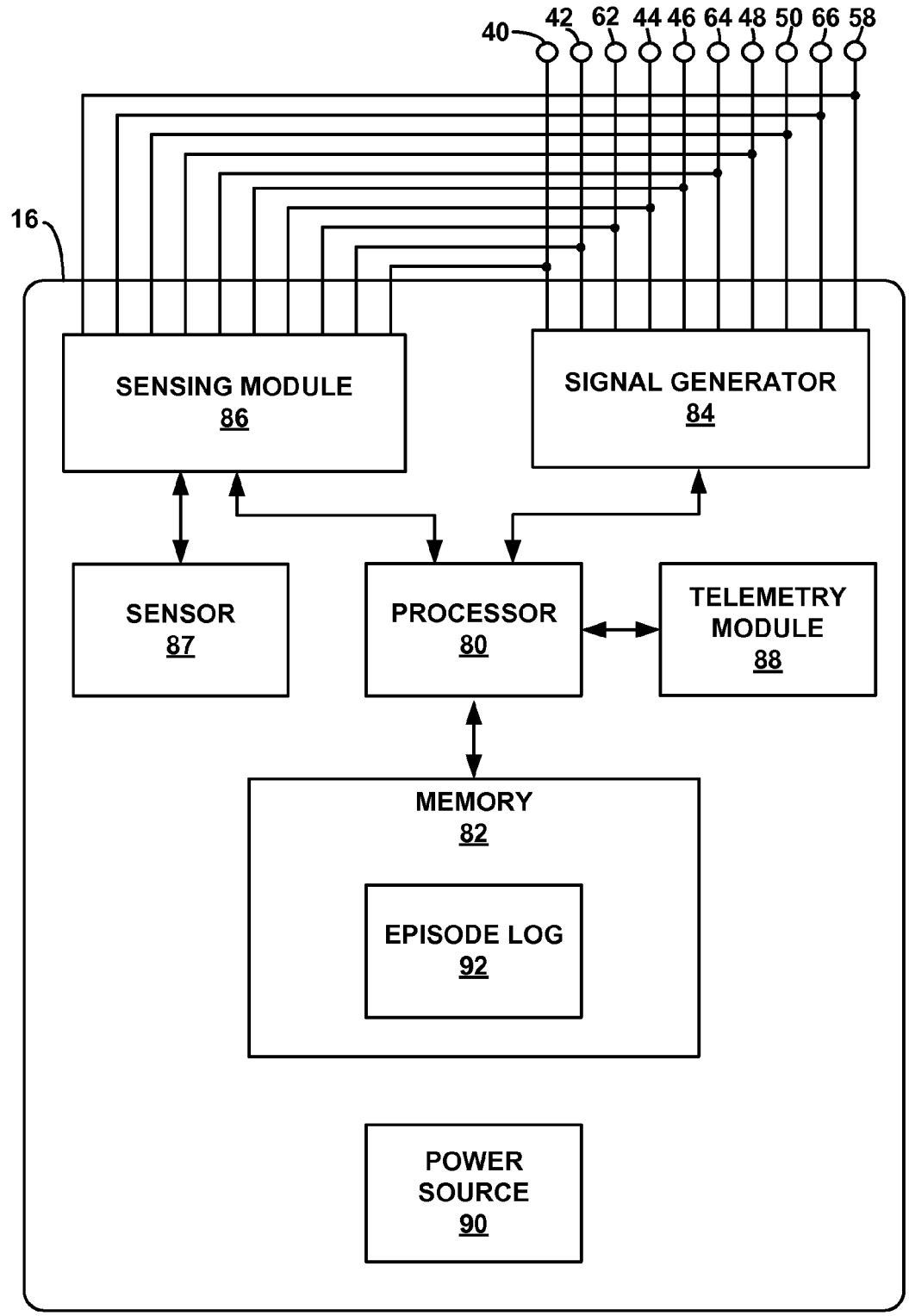
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, sensing module 86, sensor 87, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver therapeutic electrical signals to heart 12 according operational parameters stored in memory 82. For example, processor 80 may control signal generator 84 to deliver electrical pulses with the amplitudes, pulse widths, frequency, or electrode polarities specified by the operational parameters.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver therapeutic electrical signals to heart 12. For example, signal generator 84 may deliver defibrillation shocks to heart 12 via at least two electrodes 58, 62, 64, 66. Signal generator 84 may deliver pacing stimulation via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation signals in the form of electrical pulses. In other examples, signal generator may deliver one or more of these types of therapeutic electrical signals in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation shocks or pacing stimulation. The switch module may include a switch array, switch matrix, multiplexer, or any other type of switching device suitable to selectively couple the therapeutic electrical signal to selected electrodes.

Sensing module 86 monitors signals from at least one of electrodes 40, 42, 44, 46, 48, 50, 58, 62, 64 or 66 in order to monitor electrical activity of heart 12. Sensing module 86 may also include a switch module to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86. Processor 80 may control the functionality of sensing module 86 by providing signals via a data/address bus.

Sensing module 86 may include one or more detection channels, each of which may comprise an amplifier. The detection channels may be used to sense the cardiac signals. Some detection channels may detect events, such as R- or P-waves, and provide indications of the occurrences of such events to processor 80. One or more other detection channels may provide the signals to an analog-to-digital converter, for processing or analysis by processor 80. In response to the signals from processor 80, the switch module within sensing module 86 may couple selected electrodes to selected detection channels.

For example, sensing module 86 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 80 then uses that detection in measuring frequencies of the sensed events. Different narrow band channels of sensing module 86 may have distinct functions. For example, various narrow band channels may be used to sense either atrial or ventricular events.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a wide band channel which may comprise an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) provided by, for example, sensing module 86 or processor 80. In some examples, processor 80 may store the digitized versions of signals from the wide band channel in memory 82 as EGMs.

In some examples, processor 80 may employ digital signal analysis techniques to characterize the digitized signals from the wide band channel to, for example detect and classify the patient's heart rhythm. Processor 80 may detect and classify the patient's heart rhythm by employing any of the numerous signal processing methodologies known in the art.

Processor 80 may maintain programmable interval counters. For example, if IMD 16 is configured to generate and deliver pacing stimulation to heart 12, processor 80 may maintain programmable counters which control the basic time intervals associated with various modes of pacing, including anti-tachycardia pacing (ATP) and pacing associated with cardiac resynchronization therapy (CRT). Intervals maintained by processor 80 for pacing may include atrial and ventricular pacing escape intervals, refractory periods during which sensed P-waves and R-waves are ineffective to restart timing of the escape intervals, and, in examples in which pacing stimulation comprises pulses, the pulse widths of the pacing pulses. As another example, processor 80 may define a blanking period, and provide signals to sensing module 86 to blank one or more channels, e.g., amplifiers, for a period during and after delivery of a therapeutic electrical signal to heart 12. The durations of these intervals may be determined by processor 80 in response to stored data in memory 82. Processor 80 may also determine the amplitude of the cardiac pacing stimulation.

In some examples, processor 80 resets interval counters upon sensing of R-waves and P-waves with detection channels of sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing stimulation to one of the chambers of heart 12. Processor 80 may reset the interval counters upon the generation of pacing stimulation by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a suspected tachyarrhythmia event, such as ventricular fibrillation or ventricular tachycardia. In some examples, a portion of memory 82 may be configured as a plurality of recirculating buffers, capable of holding series of measured intervals, which may be analyzed by processor 80 to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No.

5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples. Processor 80 may detect a fast-rate NS episode if the interval length falls below a threshold, but is not detected for the number of cycles necessary for classification as a tachyarrhythmia or fibrillation.

IMD 16 may comprise one or more sensors, such as sensor 87 illustrated in the example of FIG. 4. Sensor 87 may be within housing 60 (FIG. 2) of IMD 16. IMD 16 may additionally or alternatively be coupled to one or more sensors located outside of housing 60 of IMD 16. Sensor 87 may be located on or within on or more of leads 18, 20 and 22, or another lead which may or may not include stimulation/sensing electrodes. In some examples, sensor 87 may be separately housed from IMD 16, and may be coupled to IMD 16 via wireless communication. Sensor 87 may be implanted or external.

Sensor 87 may comprise, as examples, a pressure sensor, a motion sensor, a heart sound sensor, or any sensor capable of generating a signal that varies as a function of mechanical activity, e.g., contraction, of heart 12. A pressure sensor may be, for example, a capacitive pressure sensor that senses an intracardiac or other cardiovascular pressure. A motion sensor may be, for example, an accelerometer or piezoelectric element. Sensing module 86 may receive one or more signals from sensor 87 or a plurality of sensors, e.g., in addition or alternative to receiving one or more signals from electrodes 40, 42, 44, 46, 48, 50, 58, 62, 64 or 66. Sensing module 86 may monitor, among other things, the mechanical activity of heart 12 based on such signals.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., EGM signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Processor 80 may store cardiac EGMs for physiological episodes, such as tachyarrhythmias, in memory 82. For example, processor 80 may store cardiac EGMs for atrial and ventricular tachycardia and fibrillation episodes, in response to the detection of the tachycardia or fibrillation using any of the techniques described above. The EGM may include data collected by sensing module 86 during detection of the tachyarrhythmia, as well as after detection, e.g., during treatment of the tachyarrhythmia. The data stored for the episode may also include a marker channel associated with the EGM. The marker channel may annotate the EGM with events detected by sensing module 86, such as ventricular or atrial depolarizations, as well an indication of when during the episode a responsive therapy was delivered by signal generator 84.

Processor 80 may also store cardiac EGMs for high-rate NS episodes within memory 82, in response to detection of the high-rate NS episodes. The data stored for a high-rate NS episode may also include a marker channel associated with the EGM. Memory 82 may include a dedicated storage space, such as episode log 92, to store high-rate NS episode data. Episode log 92 may have a limited size and may only have the capacity to store data associated with a predetermined number of high-rate NS episodes. Memory 82 may also include other divisions and dedicated storage spaces, e.g., for storage of physiological event data, such as EGMs and marker channels associated with tachycardia and fibrillation episodes.

Data corresponding to sensed high-rate NS episodes that occur close in time to detection of a lead integrity condition may help facilitate assessment of a lead in response to the detection of the lead integrity condition. Therefore, processor 80 may implement techniques for storing data corresponding to high-rate NS episodes that occur close in time to detection of a lead integrity condition. When processor 80 detects a high-rate NS episode or a lead integrity condition, processor 80 may automatically adjust its data storage operation to provide more diagnostic data regarding the lead integrity condition. More specifically, processor 80 may implement a high-rate NS episode storage operation configured to store data associated with episodes that occur proximate to detection of a lead integrity condition.

For example, processor 80 may detect a high-rate NS episode, e.g., based on signals sensed by sensing module 86, and activate high-rate NS data storage in response to the detection. Processor 80 may store data associated with high-rate NS episodes in episode log 92 in chronological order. If episode log 92 reaches capacity, the data associated with the oldest episode may be discarded such that data associated with the most recent episode may be stored, e.g., in a first-in-first-out (FIFO) manner. When processor 80 detects a lead integrity condition, the data storage operation may prevent the data stored in episode log 92 from being overwritten until the data is accessed for analysis, e.g., via programmer 24. This may help ensure that data preceding the detection of the lead integrity condition is available for assessment of the lead integrity condition.

In some examples, the data stored in episode log 92 may be accessed by more than one user, such as a clinician in the emergency department and a principle following clinician. To help ensure that data stored in episode log 92 is available for assessment by each of the appropriate users, a user may verify that the data stored in episode log 92 may be overwritten after the data is accessed. As an alternative, the data stored in episode log 92 may automatically be downloaded to a network, such as the Medtronic CareLink® Network developed by Medtronic, Inc., of Minneapolis, Minn., or some other network linking patient 14 to a clinician, e.g., in response to a detection of a lead integrity condition, when the episode log is full after detection of a lead integrity condition, or when the data stored in episode log 92 is accessed for analysis.

As another example, multiple use accounts may be used to manage information stored in episode log 92. The techniques may include authenticating a user as a general user or as one of a set of authenticable users. In some examples, the general user may perform a subset of the actions that may be performed by an authenticable user, such as only being able to clear information from the general user account. In this manner, even if data in episode log 92 is cleared from a general user account, one or more authenticable users may still access the data stored in episode log 92. Techniques for managing information stored in an implantable medical device system by using multiple user accounts are described in further details in U.S. patent application Ser. No. 12/493,889 to Theodore Chow, which was filed on Jun. 29, 2009 and is entitled, "MULTIPLE USER ACCOUNTS FOR MANAGING STORED INFORMATION IN AN IMPLANTABLE MEDICAL DEVICE SYSTEM," and is incorporated herein by reference in its entirety.

If episode log 92 is not at capacity when processor 80 detects the lead integrity condition, processor 80 may continue storing high-rate NS episode data until episode log 92 is at capacity or the data is accessed for analysis, e.g., via programmer 24. Data stored following the detection of a lead integrity condition may also help facilitate evaluation of the lead integrity condition. If the high-rate NS data storage operation is activated for a threshold time period, e.g., one month, without detection of a lead integrity condition, processor 80 may turn the high-rate NS data storage operation off.

Additionally or alternatively, processor 80 may activate the high-rate NS data storage operation in response to detection of a lead integrity condition. Processor 80 may store data associated with high-rate NS episodes in episode log 92 subsequent to the detection of the lead integrity condition. Processor 80 may store such episode data until episode log 92 reaches capacity or the data is accessed for analysis, e.g., via programmer 24. If episode log 92 reaches capacity, processor 80 may prevent the stored data from being overwritten until the data is accessed for analysis.

Processor 80 may periodically or continuously monitor lead integrity. If processor 80 detects a lead integrity condition, processor 80 may trigger a lead integrity alert. A lead integrity alert may provide advance warning of a potential lead fracture or other lead integrity condition based on lead impedance, the frequency of high-rate NS episodes, and/or the frequency of short intervals counted on a sensing integrity counter.

Processor 80 may make one or more impedance measurements of one or more electrical paths to monitor lead integrity. Each electrical path may include a plurality of electrodes (e.g., electrodes 40, 42, 44, 46, 48, 50, 58, 62, 64 or 66). An electrical path for which impedance is measured may include the electrodes used to sense cardiac electrical signals. In some examples, processor 80 may measure electrical parameter values during delivery of an electrical signal between at least two of the electrodes. Processor 80 may control signal generator 84 to deliver the electrical signal between the electrodes. Processor 80 may determine impedance values based on parameter values measured by sensing module 86. In particular, an analog-to-digital converter may digitize parameter values measured by sensing module 86, and processor 80 may determine impedance values based on the digitized parameter values and store the impedance values in memory 82.

In some examples, processor 80 may perform an impedance measurement by controlling delivery, from signal generator 84, of a voltage pulse between first and second electrodes. Sensing module 86 may measure a resulting current, and processor 80 may calculate a resistance based upon the voltage amplitude of the pulse and the measured amplitude of the resulting current as digitized by an analog-to-digital converter. In other examples, processor 80 may perform an impedance measurement by controlling delivery, from signal generator 84, of a current pulse between first and second electrodes. Sensing module 86 may measure a resulting voltage, and processor 80 may calculate a resistance based upon the current amplitude of the pulse and the measured amplitude of the resulting voltage as digitized by an analog-to-digital converter. Sensing module 86 may include circuitry for measuring amplitudes of resulting currents or voltages, such as sample and hold circuitry.

In these examples of performing impedance measurements, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may collect impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components. Impedance data may include actual, measured impedance values, or may include values that can be used to calculate impedance (such as current and/or voltage values).

In one embodiment, processor 80 may analyze the measured impedance values, and may compare these values, or other computed values, to determined thresholds and identify any possible conditions with one or more electrical paths that include two or more of the electrodes. For example, processor 80 may, as a result of one or more comparisons, determine that one or more of leads 18, 20, and 22 has a lead-related condition, or more specifically that one or more electrodes or associated conductors within the leads may have an integrity condition. In some examples, processor 80 determines trends of impedance measurements, or statistical or other processed values determined based on impedance measurements to determine whether a lead integrity condition is present.

In one example, processor 80 may detect a lead integrity condition if at least two of the following criteria are met within the past 60 days: a lead impedance measurement is less than approximately 50% or greater than approximately 175% of a baseline impedance value, a sensing integrity counter is incremented by at least approximately 30 within a period of three consecutive days or less, or sensing module 86 detects at least two high-rate NS episodes with a 4-beat average cardiac interval of less than approximately 220 milliseconds. However, any lead integrity criteria may be utilized to detect a lead integrity condition. In some examples, processor 80 adjusts tachyarrhythmia detection settings and diagnostic settings to avoid delivery of an inappropriate shock and/or provides an audible, visible and/or vibrational alert as a lead integrity alert, e.g., via an element of IMD 16 or programmer 24, in response to detecting a lead integrity condition.

In some examples, IMD 16 may signal programmer 24 to further communicate, or programmer 24 may independently further communicate with and pass a lead integrity alert and associated high-rate NS episode data through a network such as the Medtronic CareLink® Network developed by Medtronic, Inc., of Minneapolis, Minn., or some other network linking patient 14 to a clinician.

Figure 5:
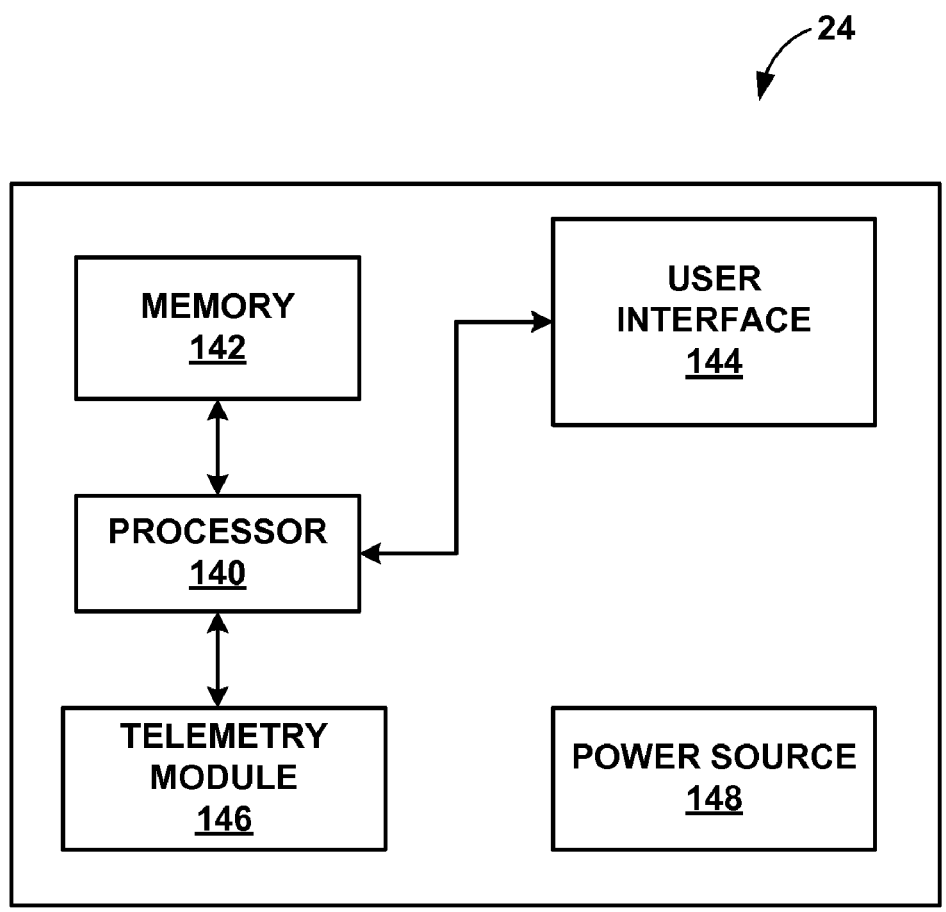
FIG. 5 is a functional block diagram of an example configuration of the external programmer shown in FIG. 1, which facilitates user communication with an IMD.

FIG. 5 is a block diagram of an example programmer 24. As shown in FIG. 5, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select operational parameters, e.g., therapy and monitoring parameters, generate new parameters, modify parameters, or transmit the parameters to a medical device, such as IMD 16 (FIG. 1). The clinician may interact with programmer 24 via user interface 144 which may include display to present graphical user interface to a user, and a keypad or another mechanism for receiving input from a user.

Processor 140 can take the form one or more microprocessors, DSPs, ASICs, FPGAs, programmable logic circuitry, or the like, and the functions attributed to processor 140 herein may be embodied as hardware, firmware, software or any combination thereof. Processor 140 of programmer 24 may provide any of the functionality ascribed herein to processor 80 of IMD 16, or otherwise perform any of the methods described herein.

Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 4).

Telemetry module 142 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Figure 6:
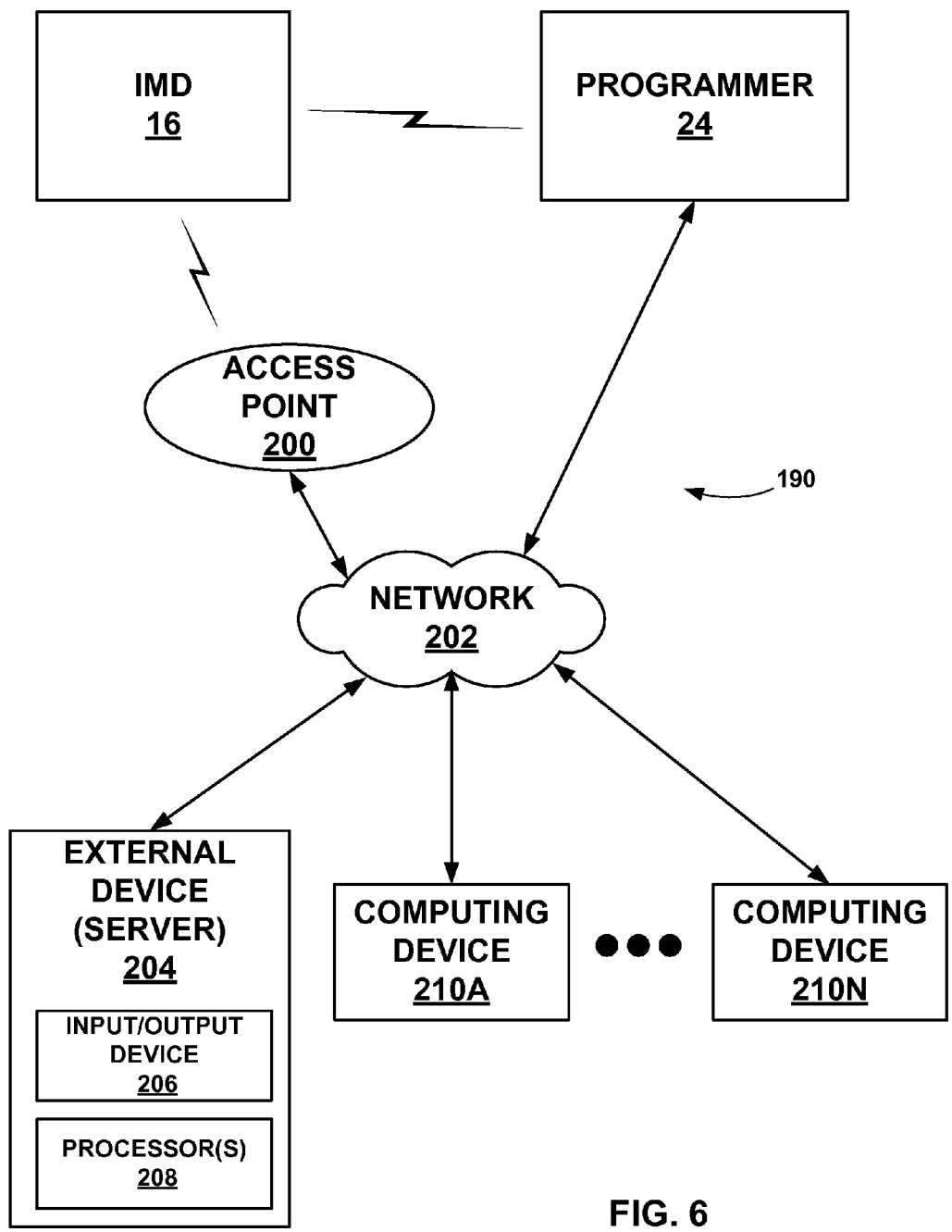
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system 190 that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communicate with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein. For example, as illustrated in FIG. 6, server 204 may comprise one or more processors 208 and an input/output device 206, which need not be co-located.

Server 204 may, for example, practice the methods described herein for storing an EGM (and in some cases a marker channel) for a high-rate NS episode. Server 204 may store EGMs (and in some cases marker channels) within episode logs 92 maintained by server 204. Furthermore, in some examples in which IMD 16 controls the data storage operation for high-rate NS episodes as described above, server 204 may provide a database or other memory for storing the EGMs (and in some cases a marker channels). IMD 16 may store EGMs within an external storage unit or memory, which may be provided by server 204 as one example, or programmer 24 as another.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some embodiments, server 204 or one or more of the computing devices 210A-210N may perform any of the various functions or operations described herein.

Network 202 may comprise a local area network, wide area network, or global network, such as the Internet. In some cases, programmer 24 or server 204 may assemble episode log 92 and other sensing integrity information in web pages or other documents for viewing by and trained professionals, such as clinicians, via viewing terminals associated with computing devices 210A-210N. System 190 may be implemented, in some aspects, with general network technology and functionality similar to that provided by the Medtronic CareLink® Network developed by Medtronic, Inc., of Minneapolis, Minn.

Figure 7:
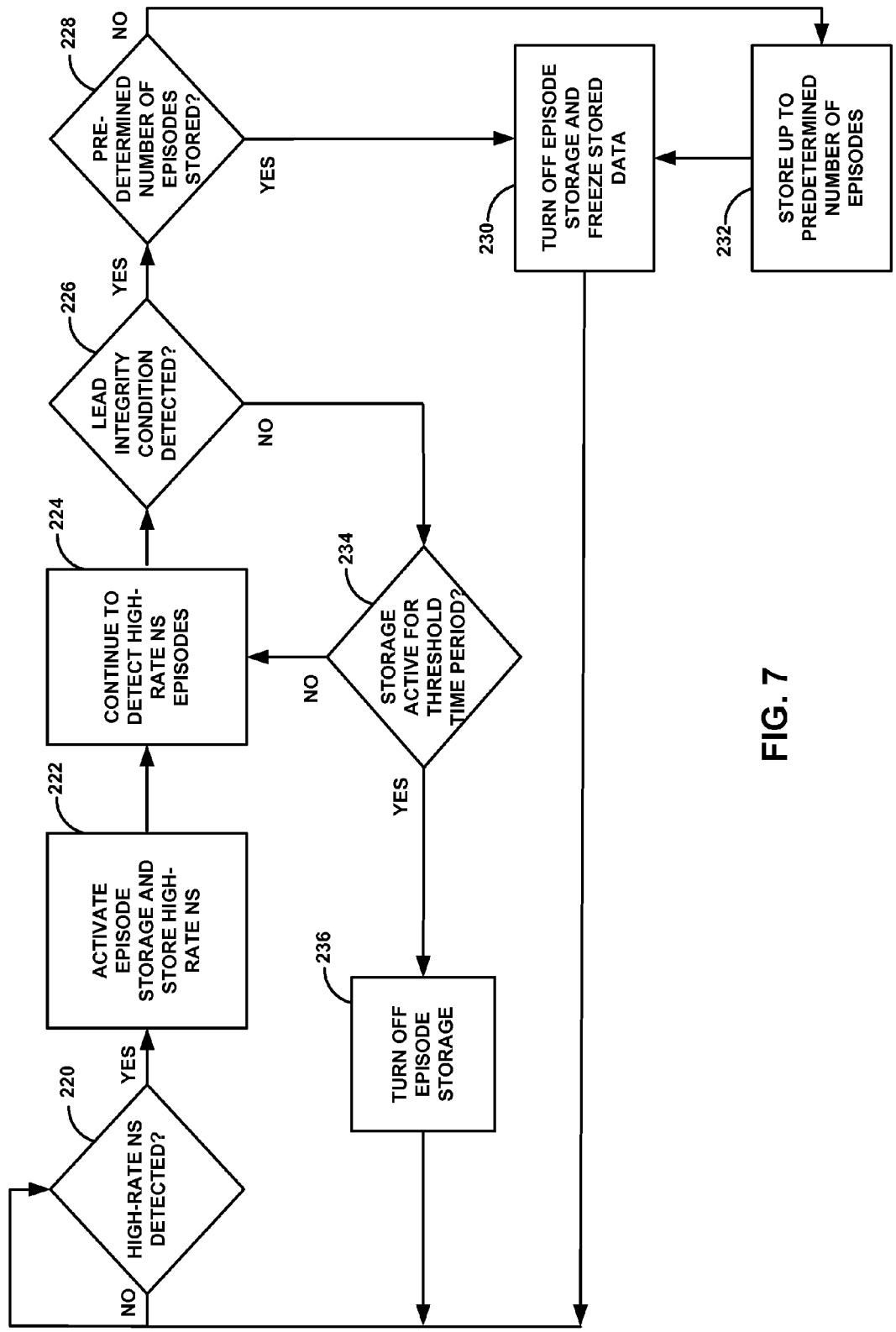
FIG. 7 is a flow diagram of an example method of storing high-rate NS episode data for evaluation of a lead integrity condition.

FIG. 7 is a flow diagram of an example method of storing high-rate NS episode data for evaluation of a lead integrity condition. The functionality described with respect to FIG. 7 as being provided by a particular processor or device may, in other examples, be provided by any one or more of the processors or devices described herein.

Sensing module 86 may monitor signals from heart 12, and processor 80 may determine whether a high-rate NS episode has occurred based on, for example, the rate of sensed cardiac events, e.g., depolarizations, detected by sensing module 86 (220). High-rate NS episodes may comprise a series of rapid events detected by sensing module 86 as ventricular or atrial depolarizations, which series of events did not meet a criterion or criteria for classification as a tachycardia or fibrillation. A high-rate NS episode may fail to meet a criterion for classification as a tachycardia or fibrillation if, for example, the episode was too short to meet a number of intervals to detect (NID) threshold for tachycardia or fibrillation.

If processor 80 detects a high-rate NS episode, processor 80 may activate storage of high-rate NS episode data and store data associated with the high-rate NS episode within memory 82 (222). In some examples, memory 82 stores cardiac data, such as EGMs, corresponding to the high-rate NS episode, and may also store a marker channel associated with the EGM. The marker channel may annotate the EGM with events detected by sensing module 86, such as events detected as ventricular or atrial depolarizations.

Once the high-rate NS episode storage is activated, processor 80 may continue to detect high-rate NS episodes and store data associated with these episodes in memory 82 (224). Memory 82 may include a dedicated storage space, such as episode log 92, to store high-rate NS episode data. Episode log 92 may have a limited size and may only have the capacity to store data associated with a predetermined number of high-rate NS episodes. Processor 80 may store data associated with high-rate NS episodes in chronological order. If episode log 92 reaches capacity, the oldest data may be discarded such that data associated with the most recent high-rate NS episodes are stored.

Processor 80 may also determine whether a lead integrity condition has been detected (226). Processor 80 and/or sensing module 86 may detect a lead integrity condition based on lead impedance, the frequency of high-rate NS episodes, and the frequency of short ventricular intervals counted on a sensing integrity counter. Processor 80 may periodically or continuously monitor lead integrity, e.g., concurrently with detecting high-rate NS episodes (220, 224).

If a lead integrity condition is detected, processor 80 may determine whether memory 82 contains data associated with a predetermined number of high-rate NS episodes (228). The predetermined number may correspond to the number of high-rate NS episodes that the portion of memory 82 dedicated to storing high-rate NS episode data, e.g., episode log 92, has the capacity to store data for.

If memory 82 contains data associated with the predetermined number of high-rate NS episodes, processor 80 may turn off storage of high-rate NS episodes and prevent the stored high-rate NS episode data from being overwritten until the data is accessed for analysis, e.g., via programmer 24 (230). If memory 82 contains data associated with fewer than the predetermined number of high-rate NS episodes, processor 80 may continue to detect high-rate NS episodes and store data associated with the episodes within memory 82 until the number of high-rate NS episodes for which data is stored reaches the predetermined number or the data is accessed for analysis, e.g., via programmer 24 (232). If the number of high-rate NS episodes for which data is stored reaches the predetermined number before the data is accessed for analysis, processor 80 may turn off storage of high-rate NS episode data and prevent the stored high-rate NS episode data from being overwritten until the data is accessed for analysis, e.g., via programmer 24 or a network, such as the Medtronic CareLink® Network developed by Medtronic, Inc., of Minneapolis, Minn. or some other network linking patient 14 to a clinician (230). The data may accessed automatically, e.g., according to a schedule, or manually, e.g., in response to a request. The data may be accessed wirelessly or via a wired connection.

Processor 80 may also determine if the high-rate NS episode data storage has been active for a threshold period of time without the detection of a lead integrity condition (234). In some examples, processor 80 may activate a timer when it activates storage of high-rate NS episode data (222). Processor may monitor the timer to determine whether a threshold period of time has elapsed without the detection of a lead integrity condition (234). Processor 80 may turn off storage of high-rate NS episode data if the threshold time period has elapsed without detection of a lead integrity condition (236). Turning off storage of high-rate NS episode data storage may help conserve power, e.g., of power source 90. Storage of high-rate NS episode data may be reactivated at a later time, e.g., in response to detection of a high-rate NS episode (220).

Figure 8:
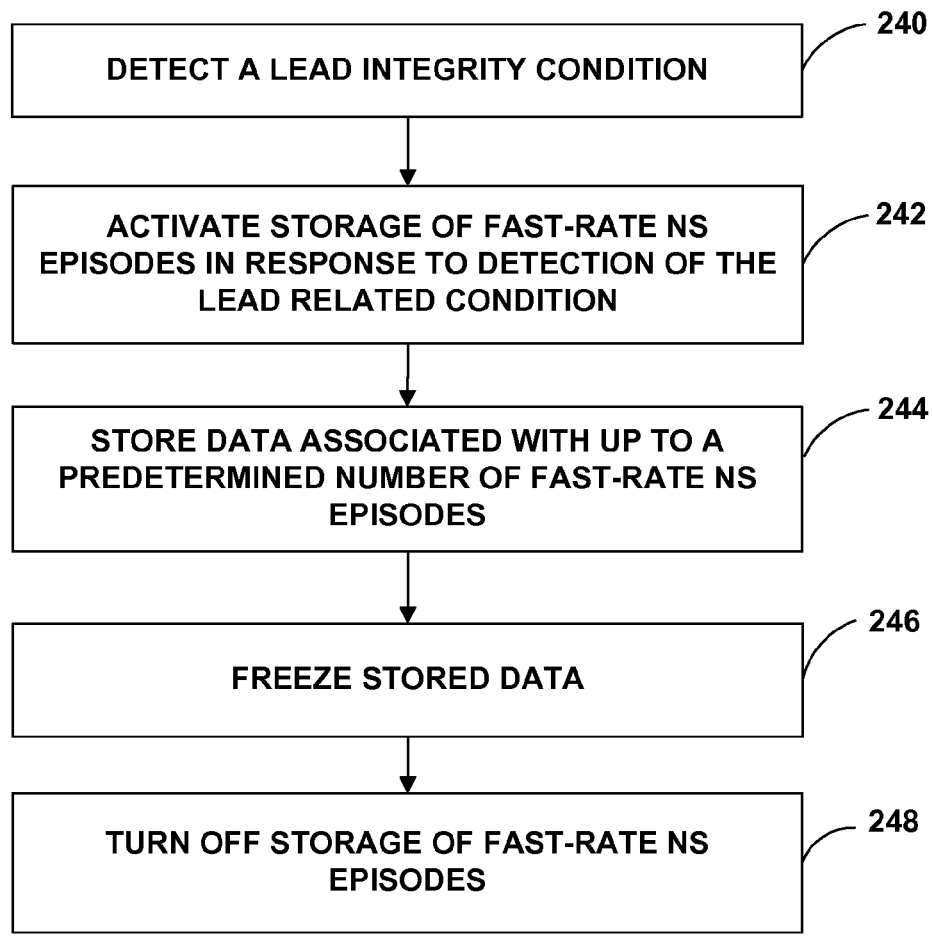
FIG. 8 is a flow diagram of another example method of storing high-rate NS episode data for evaluation of a lead integrity condition.

FIG. 8 is a flow diagram of another example method of storing fast rate-NS episode data for evaluation of a lead integrity condition. The functionality described with respect to FIG. 8 as being provided by a particular processor or device may, in other examples, be provided by any one or more of the processors or devices described herein.

Processor 80 may detect a lead integrity condition, e.g., based on lead impedance, the frequency of high-rate NS episodes, and/or the frequency of short ventricular intervals counted on a sensing integrity counter (240). Processor 80 may activate storage of high-rate NS episode data upon detection of the lead integrity condition (242). Data stored following the lead integrity condition may help facilitate evaluation of the lead related condition.

Processor 80 may store data associated with up to a predetermined number of high-rate NS episodes (244). The predetermined number of episodes may correspond to the capacity of a dedicated storage space for high-rate NS episode data, such as episode log 92. If the episode log reaches capacity, the data storage operation may prevent the stored data from being overwritten until the data is accessed for analysis (246) and turn off storage of additional fast rate-NS episode data (248). If the data is accessed for analysis, e.g., via programmer 24, before the number of high-rate NS episodes for which data is stored reaches the predetermined number, processor 80 may turn off storage of high-rate NS episode data after the data is accessed for analysis (248).

The methods of storing fast rate-NS episode data for evaluation of a lead integrity condition of FIGS. 7 and 8 may be used in conjunction. For example, processor 80 may monitor for high-rate NS episodes and lead integrity conditions simultaneously. If a high-rate NS episode is detected, processor 80 may follow the method of FIG. 7, and if a lead integrity condition is detected, processor 80 may follow the method of FIG. 8.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A system comprising:
a sensing module that monitors a signal indicative of cardiac contractions;
a processor that detects a first high rate non-sustained episode based on the signal sensed by the sensing module and activates a data storage operation for storing data associated with high rate non-sustained episodes in response to detecting the first episode; and
a memory that stores data associated with the first episode in response to the processor activating the data storage operation, wherein the processor detects a lead integrity condition based on the signal sensed by the sensing module and determines whether the memory contains data associated with a predetermined number of high rate non-sustained episodes, and wherein the processor determines that the memory contains data associated with the predetermined number of high rate non-sustained episodes, turns off the data storage operation in response to the determination, and prevents data stored in the memory from being overwritten until the data is accessed for analysis.

2. The system of claim 1, wherein the processor detects a second high rate non-sustained episode based on the signal sensed by the sensing module and the memory stores data associated with the second episode in response to the processor detecting the second episode.

3. The system of claim 1, wherein the processor determines that the memory contains data associated with less than the predetermined number of high rate non-sustained episodes, the processor detects an additional high rate non-sustained episode based on the signal sensed by the sensing module, and the memory stores data associated with the additional episode in response to the processor detecting the additional episode.

4. The system of claim 1, wherein the processor determines that the data storage operation has been active for a threshold time period and turns off the data storage operation in response to determining that the data storage operation has been active for the threshold time period.

5. The system of claim 1, wherein the data associated with the first episode comprises an electrogram signal sensed by the sensing module.

6. The system of claim 5, wherein the data associated with the first episode further comprises a marker channel associated with the electrogram.

7. The system of claim 1, further comprising an implantable medical device that comprises the sensing module.

8. The system of claim 7, wherein the implantable medical device comprises the processor.

9. The system of claim 7, wherein the implantable medical device comprises at least one of a pacemaker, cardioverter, or defibrillator.

* * * * *